United States Patent [19]

O'Lenick, Jr.

[11] Patent Number: 5,907,049

[45] Date of Patent: May 25, 1999

[54] MEADOWFOAM AMINE OXIDES

[75] Inventor: Anthony J. O'Lenick, Jr., Lilburn, Ga.

[73] Assignee: Fan Tech LTD, Chicago, Ill.

[21] Appl. No.: 09/075,444

[22] Filed: May 11, 1998

Related U.S. Application Data

[63] Continuation-in-part of application No. 08/847,202, May 1, 1997, Pat. No. 5,834,576.

[51] Int. Cl.$^6$ .................................................. C07C 233/00

[52] U.S. Cl. .............................. 554/55; 554/51; 514/613; 514/626; 514/642

[58] Field of Search ......................... 584/51, 55; 514/613, 514/624, 642

*Primary Examiner*—Gary Geist
*Assistant Examiner*—Deborah D. Carr

[57] ABSTRACT

The present invention deals with the composition of matter and the utilization of certain amine oxides of meadowfoam amido propyl dimethyl amine. These materials are useful in personal care applications.

3 Claims, No Drawings

MEADOWFOAM AMINE OXIDES

RELATED APPLICATIONS

This application is a continuation in part of application Ser. No. 847,202 filed May 1, 1997, now U.S. Pat. No. 5,834,576.

BACKGROUND OF THE INVENTION

1. Field of the Invention

The present invention deals with surface active compounds that are the amine oxide of meadowfoam amidopropyl dimethyl amine. The compounds of the present invention possess conditioning properties when applied to hair. The process for their use comprises contacting the hair with an effective conditioning amount of a novel amine oxide based upon meadowfoam. The term meadowfoam as used here refers to compounds derived from meadowfoam oil, meadowfoam acid or meadowfoam methyl ester. The introduction of the meadowfoam portion of the molecule into the compounds of the present invention results in improved conditioning in personal care formulations as well as improved odor stability in the formulation.

2. Description of the Art Practices

Amine oxides are known in the art. Variation of carbon chain lengths in amido amine has direct effect upon the conditioning properties of the compound. While amido amines based upon short chain fatty acids can be made, they do not produce conditioning effects on hair. The use of fatty acids having 18 or more carbon atoms result in compounds that provide conditioning. If the compounds are saturated, like stearyl amido amine oxide the aqueous product is solid. The selection of a oleyl amido amine gives a liquid product, which is highly desirable but the compound undergoes a process of oxidative instability referred to as rancidity, producing low molecular weight aldehydes with mal odor. The availability of a liquid, oxidatively stable amido amine salts that can be used in personal care systems has been elusive prior to the compounds of the present invention.

The recent availability of meadowfoam oil, with it's 20 to 22 carbon atoms and the specific location of it's double bonds, and it's reaction to make betaines results in the preparation liquid stable betaines, having outstanding emulsifying properties and are very acceptable for use in personal care applications.

None of the prior amido amine possess the critical meadowfoam carboxy moiety. Molecules of the current invention have the meadowfoam alkyl group in the surfactant.

The parent case Ser. No. 847,202 filed May 1, 1997, discloses the procedure and processes needed to make the intermediate necessary to make the compound of the present.

THE INVENTION

This invention relates the amine oxides of meadowfoam amidopropyl dimethyl amine and a process for conditioning hair which comprises contacting the hair with an effective conditioning amount of a novel amine oxide based upon meadowfoam. The term meadowfoam as used here refers to compounds derived from meadowfoam oil, meadowfoam acid or meadowfoam methyl ester. The introduction of the meadowfoam portion of the molecule into the compounds of the present invention results in improved conditioning in personal care formulations as well as improved odor stability in the formulation.

The use of meadowfoam, weather as the triglyceride, acid or methyl ester to make an meadowfoam amidopropyl dialkyl amine salt results in unique, unexpected properties in personal care applications. Specifically the salts of the present invention provide outstanding hair conditioning, and are surprisingly oxidatively stable in aqueous personal care formulations. The unique structure of the meadowfoam results in betaines with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the amine oxide having the unique distribution of the meadowfoam on the other result in superior liquidity, lubricity, and outstanding oxidative stability. The products which result from the oxidative breakdown of unstable products are generally aldehydes.

These materials have a mal odor and in addition react with fragrances and preservatives causing formulation problems.

This fact makes the products of the present invention all the more important to the formulator of personal care products.

The amido propyl amine oxiode conforms to the following structure;

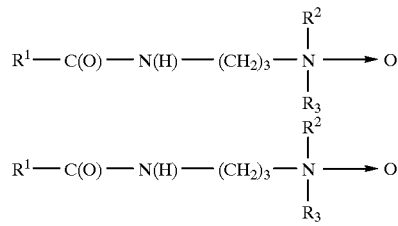

wherein:

$R^1$ is derived from meadowfoam and is;
60–65% by weight

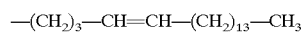

12–20% by weight a mixture of

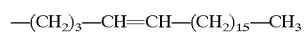

and

and
15–28% by weight

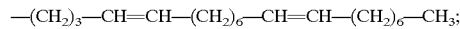

$R^2$ and $R^3$ are methyl or ethyl.

The amido amine salt is prepared in a two step reaction. The first step is the preparation of a meadowfoam amidoamine conforming to the following structure:

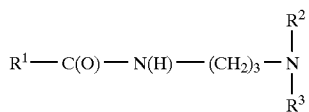

wherein:
R$^1$ is derived from meadowfoam and is;
60–65% by weight

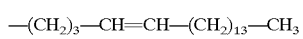

12–20% by weight a mixture of

and

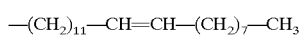

and
15–28% by weight

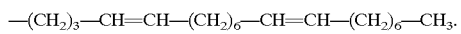

The reaction is as follows:

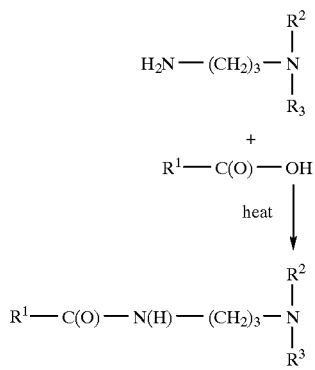

In the second reaction the amidoamine, prepared in the first reaction, is reacted in aqueous solution with an hydrogen peroxide.

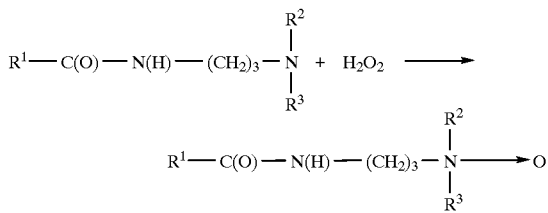

The concentration of the amido amine oxide in water is generally between 20 and 50% with 35% being preferred. Glycols, lower alcohols and other polar solvents may also be added, if desired.

EXAMPLE

Raw Materials
Meadowfoam Oil
Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Aminopropyl Amine
The compounds conform to the following structure:

Example 1
Dimethyl aminopropyl amine

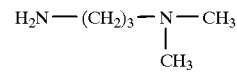

Example 2
Diethyl aminopropyl amine

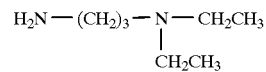

Amidoamine General Procedure—Meadowfoam Oil
To the specified number of grams the specified aminopropyl amine (Examples 1 or 2) is added 354.0 grams of meadowfoam oil. After all ingredients have been charged, under agitation, the temperature of the mass is raised to 180–200 C. This temperature is held for between 1 and 12 hours. The primary amine value decreases to vanishingly low concentrations, and the tertiary amine level becomes theoretical.

The intermediates are clear liquids and are liquid to extraordinary temperatures.

Example 3

To 122.0 grams of the specified dialkyl aminopropyl amine (Example 1) is added 354.0 grams of meadowfoam oil. After the two ingredients have been charged, under agitation, the temperature of the mass is raised to 180–200 C. and water is stripped off as formed. The primary amine value decreases to vanishingly low concentrations, and the tertiary amine level becomes theoretical.

Example 4

Example 4 is repeated, only this time 150.0 grams of the aminopropyl amine (example 2) is substituted for the aminopropyl amine of example 1.

General Procedure—Meadowfoam Fatty Acid
To the specified number of grams the specified dialkyl aminopropyl amine (Examples 1 and 2) is added 354.0 grams of meadowfoam fatty acid under agitation The temperature of the mass is raised to 180–200 C. and water is stripped off as formed. This temperature is held for between 1 and 12 hours. The acid value and the primary amine value drops to vanishingly small levels and the tertiary amine level approaches theoretical.

The products are clear liquids and are liquid to extraordinary temperatures.

Amidoamine General Procedure—Meadowfoam Oil
To the specified number of grams the specified aminopropyl amine (Examples 1 or 2) is added 354.0 grams of meadowfoam oil. After all ingredients have been charged, under agitation, the temperature of the mass is raised to 180–200 C. and water is stripped off as formed. The primary amine value decreases to vanishingly low concentrations, and the tertiary amine level becomes theoretical.

The intermediates are clear liquids and are liquid to extraordinary temperatures.

Example 5

To 102.0 grams of the specified dialkyl aminopropyl amine (Example 1) is added 354.0 grams of meadowfoam oil. After the two ingredients have been charged, under agitation, the temperature of the mass is raised to 180–200 C. and water is stripped off as formed. The primary amine value decreases to vanishingly low concentrations, and the tertiary amine level becomes theoretical.

Example 6

Example 5 is repeated, only this time 150.0 grams of the specified aminopropyl amine (example 2) is substituted for the aminopropyl amine of example 1.

The compounds are the intermediate conforming to the following structure:

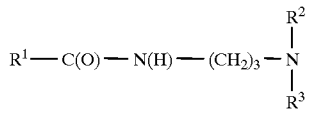

Hydrogen Peroxide

Hydrogen peroxide is an item of commerce and is available as a 50% by weight active material in water.

Amine Oxide Synthesis

To the specified 64.0 grams Of 50% $H_2O_2$ is added to the specified amount of water. The solution is heated to 80 C. and the amidoamine (examples 3–6) is added under agitation. The pH is kept between 8-9 by adding NaOH as required.

Example 7

64.0 grams of 50% peroxide is added to 520 grams of water. The solution is heated to 80 C. and 438.0 grams of amidoamine (example 3) is added under agitation. The pH is kept between 8-9 by adding NaOH as required.

Example 8–15

Example 7 is repeated, only this time the specified amount of the specified amidoamine is added, replacing the amount used in example 7 and the specified amount of water is replacing the amount specified in example 7.

| Example | Amido Amine Example | Grams | Water Grams |
|---|---|---|---|
| 8 | 3 | 438.0 | 536.0 |
| 9 | 4 | 466.0 | 1084.0 |
| 10 | 5 | 445.0 | 547.0 |
| 11 | 6 | 475.0 | 454.7 |

The products produced using the examples 7–11 are clear yellow viscous liquids. The products have outstanding oxidative stability and provide outstanding conditioning when applied to the hair.

I claim:

1. A meadowfoam amine oxide which conforms to the following structure:

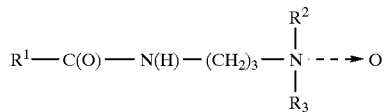

wherein:

$R^1$ is derived from meadowfoam and is:
   60–65% by weight

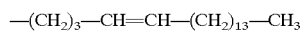

12–20% by weight a mixture of

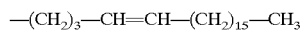

and

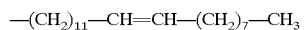

and
   15–28% by weight

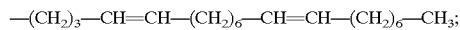

$R^2$ and $R^3$ are methyl or ethyl.

2. A meadowfoam oxide of claim 1 wherein $R^2$ is methyl.

3. A meadowfoam oxide of claim 1 wherein $R^2$ is ethyl.

* * * * *